United States Patent

Kosek et al.

[11] Patent Number: 5,527,446
[45] Date of Patent: Jun. 18, 1996

[54] GAS SENSOR

[75] Inventors: John A. Kosek, Danvers; Cecelia C. Cropley, Acton; Anthony B. LaConti, Lynnfield, all of Mass.

[73] Assignee: United States of America as represented by the Secretary of the Air Force, Washington, D.C.

[21] Appl. No.: 421,710

[22] Filed: Apr. 13, 1995

[51] Int. Cl.$^6$ ................................................. G01N 27/26
[52] U.S. Cl. .................. 205/792.5; 205/793; 205/780.5; 204/412; 204/415; 204/418; 204/421; 204/424; 204/431; 204/432
[58] Field of Search ...................... 204/431, 432, 204/412, 409, 415, 418, 421, 424, 153.14, 153.16, 153.17, 153.18; 422/83, 90, 98

[56] References Cited

U.S. PATENT DOCUMENTS

| | | | |
|---|---|---|---|
| Re. 31,915 | 6/1985 | Oswin et al. | 204/432 |
| 3,859,191 | 1/1975 | Frant et al. | 204/195 P |
| 4,013,522 | 3/1977 | Nischik et al. | 204/153.16 |
| 4,595,486 | 6/1986 | Schmidt et al. | 204/431 |
| 4,666,565 | 5/1987 | Dobson | 204/1 T |
| 4,820,386 | 4/1989 | LaConti et al. | 204/431 |
| 4,839,020 | 6/1989 | Yamaguchi et al. | 204/431 |
| 5,344,546 | 9/1994 | Kiesele et al. | 204/153.14 |

Primary Examiner—Bruce F. Bell
Attorney, Agent, or Firm—Thomas C. Stover; Stanton E. Collier

[57] ABSTRACT

A gas sensor including an electrochemical sensor cell which has a anion-exchange solid polymer electrolyte membrane with three attached electrodes is provided. The sensor cell contains no liquid electrolyte and is operated in the potentiostatic as well as the potentiodynamic modes to detect alkaline reactive gases, including vapors, such as hydrazines and derivatives thereof and ammonia. These sensor cells together with electronic circuitry, a pump and a power supply, fit into a compact, pocket-sized container to define the gas sensor of the invention which can detect traces of the above gases including 10 ppb of hydrazine and its derivatives and 10 ppm of ammonia. The invention includes the above gas sensor and the methods of operating same.

29 Claims, 5 Drawing Sheets

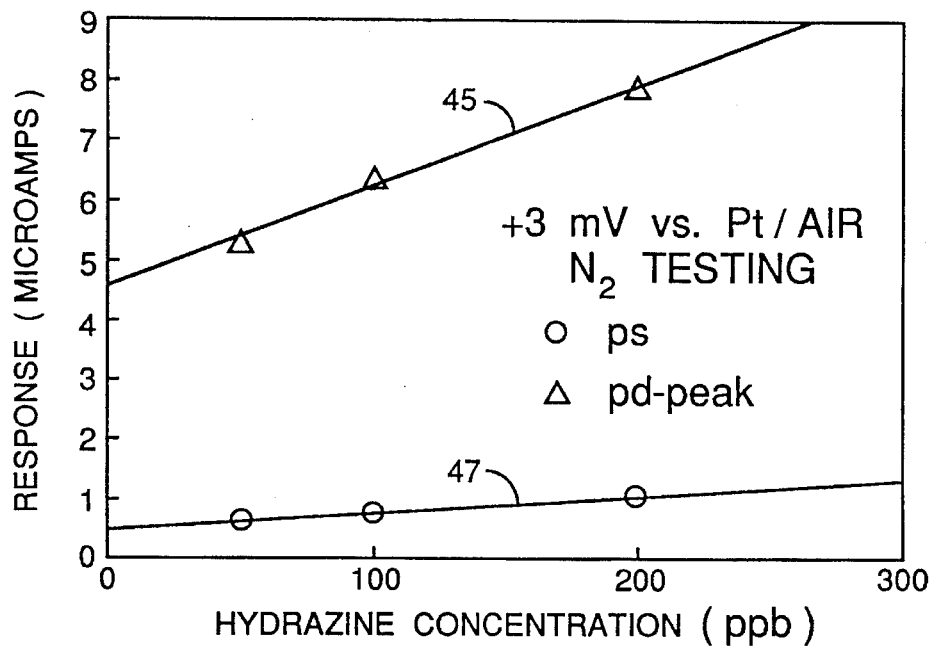
FIG. 2 COMPARISON OF Hz SENSOR CELL RESPONSE WITH Pt SENSING ELECTRODE IN THE POTENTIOSTATIC (ps) AND POTENTIODYNAMIC (pd) MODES
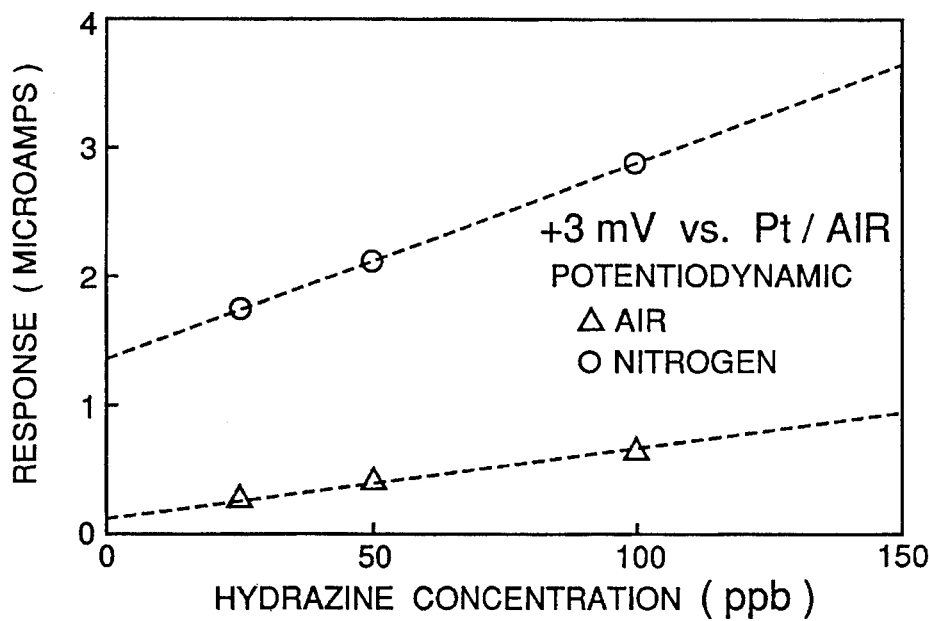
FIG. 3 COMPARISON OF SENSOR CELL WITH Pt SENSING ELECTRODE RESPONSE TO Hz IN $N_2$ AND IN AIR RESPONSE OF SENSOR CELL WITH Au SENSING
ELECTRODE TO Hz AND UDMH IN $N_2$ AND AIR

SELECTIVITY

SENSITIVITY

GAS SENSOR

STATEMENT OF GOVERNMENT INTEREST

The invention described herein may be manufactured and used by or for the Government for governmental purposes without the payment of any royalty thereon.

BACKGROUND OF THE INVENTION

1. Field of the Invention

This invention relates to a gas or vapor sensor particularly one that is highly sensitive thereto.

2. The Prior Art

To protect the health of personnel, in eg. the aerospace industry, the Air Force, NASA and the like have a need to detect low concentrations of hydrazines, toxic materials used as rocket propulsion fuels. The toxicity of hydrazine (Hz) is well known; skin and respiratory exposure can yield a wide variety of harmful effects, from nausea to carcinomas. Current recommended exposure levels (threshold limit values, TLV) set by NIOSH are 30 ppb for hydrazine (Hz), 50 ppb for monomethylhydrazine (MMH) and 60 ppb for unsymmetrical dimethylhydrazine (UDMH). However, the TLVs are expected to be reduced to 10 ppb for all three compounds in the near future. For monitoring in the field, a need exists for a reliable, inexpensive, lightweight and compact sensor capable of detecting 10 ppb Hz, MMH, and UDMH with a response time of 10 minutes or less. Also, there is a need to monitor/control other alkaline reactive gases or vapors such as ammonia in a variety of applications including aquatic, fowl and vegetable farming.

In the prior art, are gas sensor units that employ two or three electrodes and liquid electrolyte in a housing. The electrolyte is usually an alkali and can escape from its container with caustic or corrosive consequences. For examples of the prior art see U.S. Pat. No. 4,839,020 to Yamaguchi et al (1989) and U.S. Pat. No. 4,666,565 to Dobson (1987).

In other prior art U.S. Pat. No. 4,820,386 to LaConti et al (1989), discloses a cation-exchange membrane with electrodes bonded thereto in a sensor. However such sensor cannot detect certain gases or vapors that are electrochemically alkaline reactive such as hydrazine type gasses and $NH_3$. Also such sensor cell is limited to a Pt or carbon sensing electrode.

Accordingly there is a need and market for a sensor for detection of low concentrations of gas or vapors that overcomes the above prior art shortcomings.

There has now been discovered a gas or vapor sensor that avoids the use of alkaline liquid electrolyte that can leak from a container and corrode its surroundings.

Thus such sensor is durable and can detect low concentrations of gases or vapors including alkaline reactive gases as discussed below.

SUMMARY OF THE INVENTION

Broadly the present invention provides, a gas sensor comprising; an electrochemical cell having, a) an anion-exchange membrane
b) means to maintain said membrane hydrated,
c) a reference electrode,
d) a counter electrode
e) a sensing electrode and
f) a gas inlet.

The electrodes are spaced from each other and in close contact with the above membrane. Also the sensing electrode is mounted proximate an inlet in the housing to contact the gas to be detected.

In a preferred embodiment, an electric circuit is in contact with the sensing electrode and the counter electrode to conduct a current therebetween and means are mounted in such circuit to measure the current therein to derive the concentration of the gas or vapor.

In a preferred embodiment the sensing electrode and counter electrode are mounted on one side of the above membrane in contact therewith and the reference electrode is mounted on the other side of such membrane in the presence of water which hydrates the membrane.

The gas or vapor sensor embodying the present invention is particularly suited for the detection of low concentrations of reactive gases or vapors such as Hz, UDMH, MMH and ammonia as further discussed below. As used herein, "gas" includes gas or vapor.

"Alkaline reactive gas" as used herein, includes hydrazine type gas and $NH_3$.

By "hydrazine type gas" as used herein, is meant Hz, UDMH and MMH.

BRIEF DESCRIPTION OF THE DRAWINGS

The invention will become more apparent from the following detailed specification and drawings in which;

FIG. 2 is a graph of a comparison of Hz sensor response with a Pt sensing electrode in the potentiostatic and potentiodynamic modes;

FIG. 3 is a graph of a comparison of a gas sensor with a Pt sensing electrode response to Hz in $N_2$ and in air;

FIG. 11 is a fragmentary sectional elevation schematic view of the electrodes and membranes shown in FIGS. 1, 9 and 10 and FIGS. 12–21 are fragmentary schematic plan views of other electrodes-on-membrane embodiments of the invention, suitable for placing in a gas sensor cell such as shown in FIG. 1, wherein

DESCRIPTION OF PREFERRED EMBODIMENTS

Figure 1:
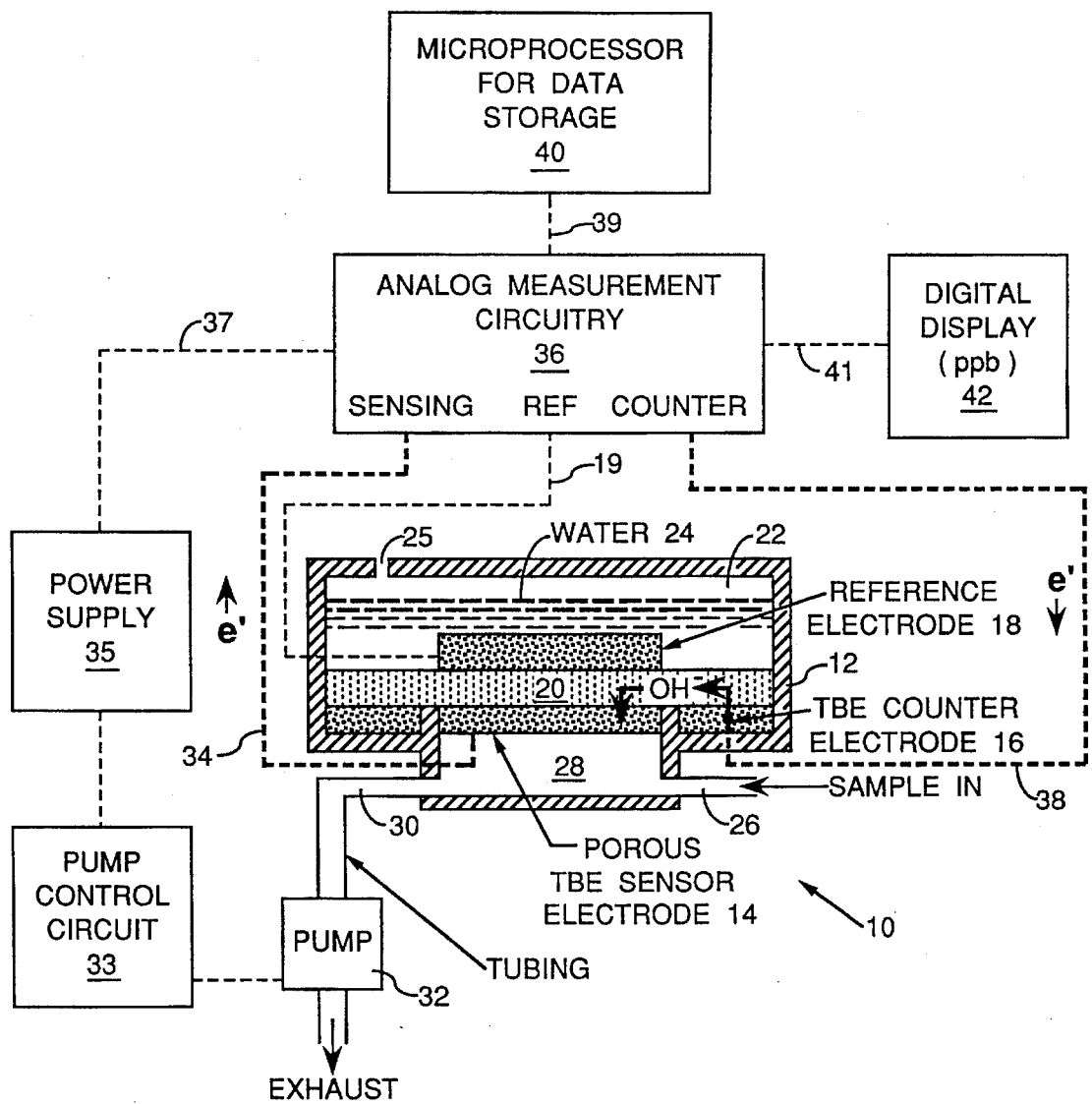
FIG. 1 is a fragmentary sectional elevation schematic view of a gas sensor and related components embodying the present invention.
Figure 7:
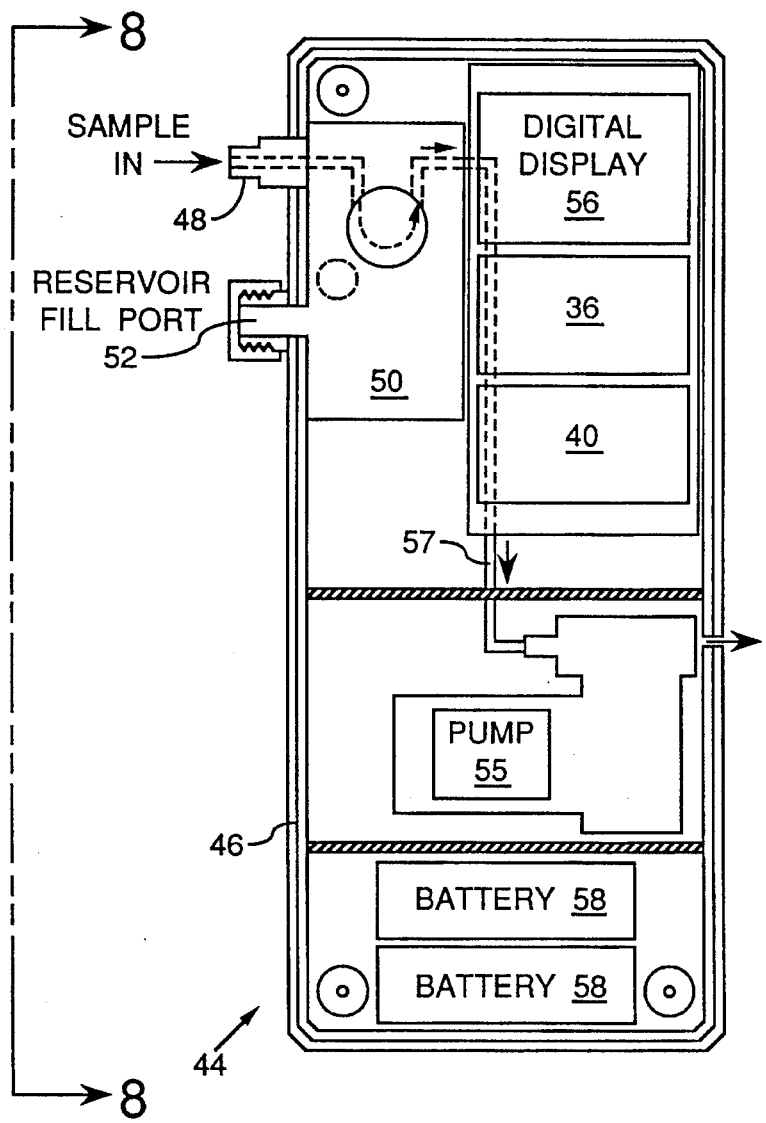
FIG. 7 is a partial sectional elevational schematic view of a gas sensor assembly embodying the present invention.
Figure 8:
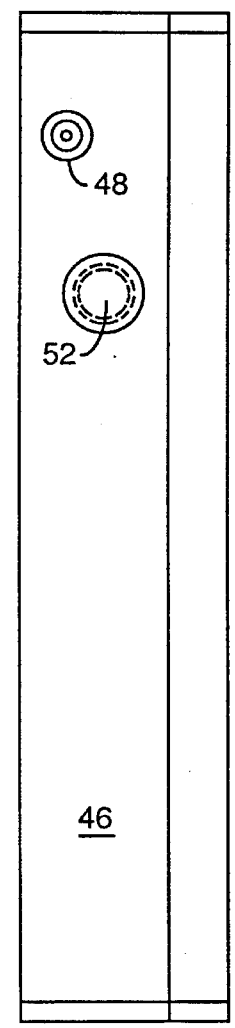
FIG. 8 is an end elevation view of the assembly of FIG. 7, taken on lines 8—8, looking in the direction of the arrows.

Referring in more detail to the drawings, particularly FIGS. 1, 7 and 8, a gas sensor cell 10, having housing 12, employs a three-electrode configuration and includes a sensing electrode 14, a counter electrode 16 and a reference electrode 18. All three electrodes are closely attached to a anion-exchange solid polymer electrolyte membrane 20, to form an integral membrane-electrode assembly (MEA). In the example of FIGS. 1 and 7, the counter electrode 16 is horseshoe-shaped and encircles the sensing electrode 14 on one side of the membrane 20 while the reference electrode 18 has about the same size and shape as the sensing electrode 14, while mounted on the other side of the membrane 20 within the housing 12, as shown in FIGS. 1, 9, 10 and 11.

The anion-exchange membrane 20 provides electrolytic contact between the above three electrodes, as indicated in FIG. 1. Such membrane preferably has a hydrocarbon backbone, radiation grafted onto a perfluorocarbon film. Such membrane 20 is the only electrolyte in the sensor cell 10 and no liquid electrolyte is present. However the membrane has been desirably soaked with hydroxide ions in solution, to provide a source for such ions and the membrane then rinsed free of solution, eg. before installation thereof, in the sensor cell of the invention.

Above the membrane 20 is a reservoir 22 which contains distilled water 24, which rests on the membrane 20 and keeps it hydrated and the $OH^-$ ions mobile, for sufficient ionic conductivity, as indicated in FIG. 1. The water 24 is replenished periodically through port 25. In this example all three electrodes have the same geometric area.

The gas to be detected can be introduced to the gas inlet chamber 28 via diffusion tube 26, flow into contact with the sensing electrode 14 and exit the sensor chamber 28 by way of exit port 30, as indicated in FIG. 1. That is the diffusion tube 26 is open to the atmosphere and the gas to be detected flows by normal gas diffusion into the inlet chamber 28 and into contact with the sensing electrode 14, as indicated in FIG. 1.

Alternatively, an intake pump 32 can be mounted to the exit port 30 and draw a sample of the gas to be detected through the diffusion tube 26 into contact with the sensing electrode 14, out the outlet port 30 and through the pump 32 as indicated in FIG. 1. The latter embodiment is preferred for ppb sampling of hydrazine type gases.

In the membrane 20 are mobile $OH^-$ ions which flow from the counter electrode through the membrane and to the sensing electrode when it detects Hz type gasses. The Hz gas reacts with the $OH^-$ ion as follows:

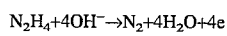

While $NH_3$ reacts with the $OH^-$ ion as follows:

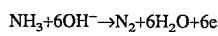

To monitor either of the above reactions, analog measurement circuitry (AMC) 36 is connected a) to sensing electrode 14, via conductor 34 and b) to counter electrode 16, via conductor 38, as shown in FIG. 1. The AMC 36 reads the current produced by the above reaction (µA) and amplifies such current and then converts it to a voltage signal (mv) which is proportional to the detected Hz concentration and provides a reading thereof on digital display 42 in ppm or preferably in ppb, as indicated in FIG. 1. Also the AMC monitors the reference electrode 18 as indicated by schematic contact line 19 in FIG. 1.

As shown in FIGS. 7 and 8, the above sensor cell and electrical components can be incorporated into a compact pocket sized unit 44, having housing 46, intake port 48, sensor cell 50, with fill port 52, AMC 36 and microprocessor 40, digital display 56, pump 55, pump line 57 and power supply 58,.

Figure 9:
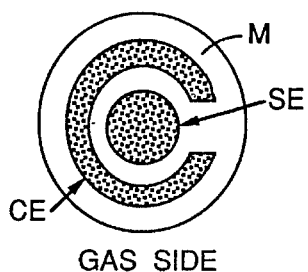
FIG. 9 is a fragmentary schematic bottom plan view of electrodes and membrane of the sensor cell of the invention shown in FIG. 1.
Figure 10:
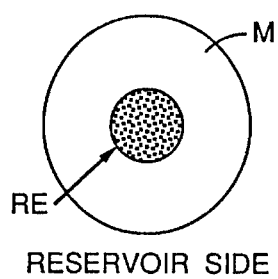
FIG. 10 is a fragmentary schematic top plan view of an electrode and membrane as shown in FIG. 1.
Figure 11:
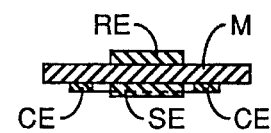

FIGS. 9, 10 and 11 show an electrolyte membrane of the invention with two electrodes attached on the gas side thereof in FIG. 9 and with a reference electrode attached to such membrane on the reservoir side thereof. The so attached components are also shown in sectional elevation in FIG. 11. As used herein, M stands for membrane, SE for sensing electrode, CE for counter electrode and RE for reference electrode. The membrane and the attached three electrodes, shown in FIGS. 9, 10 and 11, are similar to those installed in cell housing 12 of FIG. 1.

Figure 12:
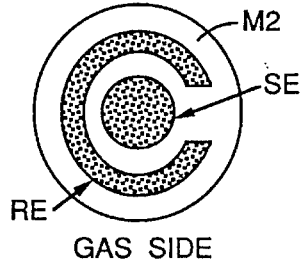
FIG. 12 shows the opposite side of the membrane from the view of FIG. 13 as does FIG. 14 to FIG. 15, FIG. 16 to FIG. 17, FIG. 18 to FIG. 19 and FIG. 20 to 21.
Figure 13:
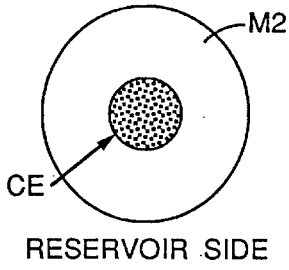

The above electrodes can be attached to the above membrane of the invention in various arrangements, within the scope of the invention, as illustrated in the embodiment of the invention shown in FIGS. 12 and 13 herein, where two electrodes are shown on the gas side of the membrane $M_2$ in FIG. 12 and the third electrode is shown on the reservoir side of M2 in FIG. 13.

Figure 14:
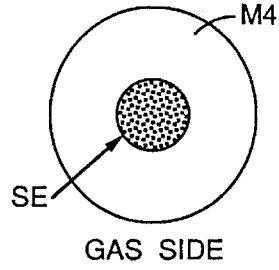
Figure 15:
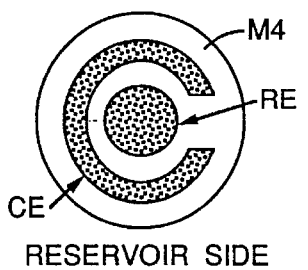
Figure 16:
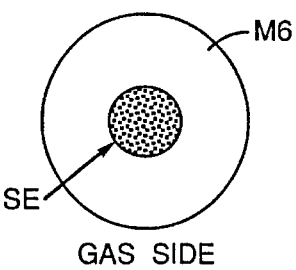
Figure 17:
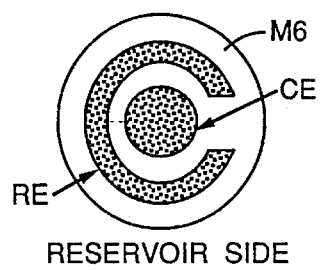
Figure 18:
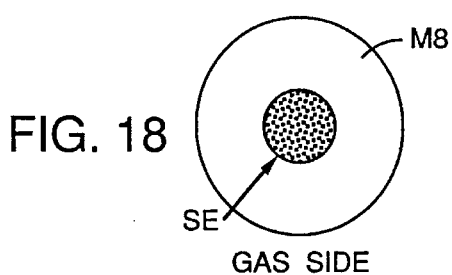
Figure 19:
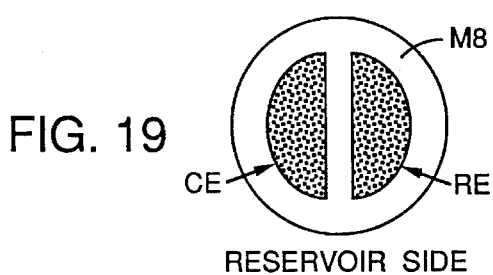
Figure 20:
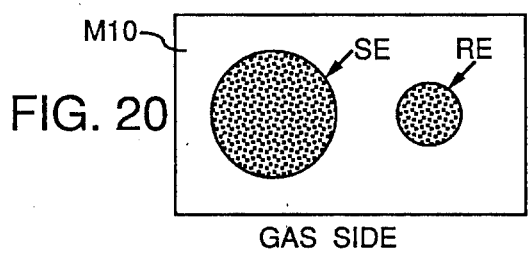
Figure 21:
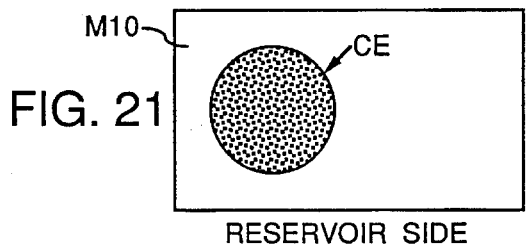

Similarly, another embodiment of the invention is shown in FIGS. 14 and 15, where the three electrodes are shown in a different arrangement on the two sides of the membrane M4. Likewise, another arrangement of the three electrodes is shown on both sides of the membrane M6 in FIGS. 16 and 17. Another arrangement of the three electrodes on both sides of the membrane MS, is shown in FIGS. 18 and 19. And still another arrangement of the three electrodes is shown on both sides of the membrane M10 in FIGS. 20 and 21. Other arrangements of the three electrodes on the membrane of the invention are possible and included within the scope of the present invention.

Thus the three-electrode sensor cell of the invention has an anion-exchange solid polymer electrolyte membrane as the only electrolyte in the system. The sensing, counter and reference electrodes are integrally attached to the membrane to form a unitized structure. The sensor cell of the invention has several inherent advantages over alkaline liquid electrolyte sensor cells previously developed for hydrazine detection, including: (a) all electrodes are intimately attached (by thermal bonding or sputtering) to the membrane, contributing to enhanced life and reliability; (b) the electrolyte is an immobilized solid polymer material, providing long life, greater stability and improved reliability; (c) the dynamic reference electrode is not subject to fracture under high shock and vibration loads; (d) the electrolyte concentration remains invariant over time, and is not affected by changes in relative humidity or subject to carbonate build-up, and (e) the only liquid present is distilled water, to keep the membrane hydrated, eliminating the use of concentrated acids or bases. Thus, cell leakage and corrosion are eliminated, providing enhanced accuracy, reproducibility, reliability and life.

The sensor cell embodying the invention, employs a platinum black/air reference electrode, which has a potential of approximately +1.05 V vs. the reversible hydrogen electrode (RHE). A platinum black counter electrode is also used. Several sensing electrode catalysts, including Pt black, gold, "Raney" Ni, Pd, Au—Pt and carbon ("Vulcan XC-72") can be employed. The choice of a sensing electrode catalyst for a given sensor cell is dependent on several factors, including desired sensitivity, selectivity and response time. For example, gold is much more selective for Hz species in the presence of $NH_3$ than Pt. For detection of $NH_3$, a Pt sensing electrode is preferred. Other catalysts, including noble metals, non-noble metals, and supported catalysts are preferred for certain applications.

A novel aspect of the sensor cell of the invention is in the use of an anion-exchange membrane as the only electrolyte in the system.

A preferred membrane is a hydrocarbon backbone radiation grafted to a perfluorocarbon film. However other anion-exchange membranes with acceptable ionic conductivity and physical properties can be used.

As indicated above, the sensor cell of the invention can be connected to suitable electronics, such as potentiostatic or potentiodynamic circuitry. Ambient air or other gas samples are desirably continuously introduced to the sensor electrode either by means of natural diffusion or by a sampling pump and the current produced by the electrochemical reaction at the sensing electrode, measured. If desired, the gas concentration can be displayed on an appropriate meter as indicated above. Visual and/or auditory alarms, set at pre-determined levels can also be incorporated. The chosen display or alarm is suitably powered by a battery and these and the sensor cell, electronics, pump (if used), are enclosed in a suitable case, eg. of pocket size.

The gas sensor cell of the invention can operate in two modes, the potentiostatic mode or the potentiodynamic mode within the scope of the invention. The potentiostatic mode of operation for a membrane cell, is known in the prior art, eg. for detecting gases such as CO and NO, per the LaConti et al reference but not for detecting hydrazine type gasses. However, the gas sensor cell embodying the invention can employ the potentiostatic method to detect hydrazine type gasses as further discussed below.

Figure 6:
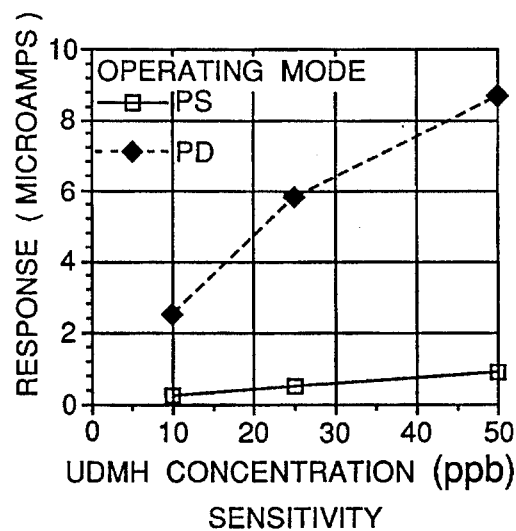
FIG. 6 is a graph of the sensitivity of a gas sensor of the invention with a Au sensing electrode in two operating modes of such cell.

In addition the gas sensor cell of the invention can be employed to detect gases using a unique method of increased sensitivity, known herein as the potentiodynamic method, as indicated in FIG. 6 and further discussed below.

The sensor cell of the invention is operated in both the potentiostatic and the potentiodynamic modes as discussed below. In a sensing instrument, the current produced by either the potentiostatic or potentiodynamic reaction is amplified and converted to a voltage signal which is proportional to the reactant concentration.

In the potentiostatic technique, the sensing electrode is held at a fixed potential (with respect to the reference electrode) at which the desired reaction of the gas to be detected occurs. The current flowing between the sensing and counter electrodes from this reaction is detected by the electronic circuitry and is a measure of the gas concentration. A three-electrode potentiostatic circuit and current amplifiers are used to operate this process. For detection of Hz species and $NH_3$, potentials in the range of +3 mV to +200 mV vs. the Pt/air reference electrode were evaluated. The preferred potential range was +3 mV to +10 mV vl the Pt/air reference electrode.

The potentiodynamic technique for sensor cell evaluation has four basic steps:

a) hold the sensing electrode potential constant to form a well-defined, potential-determined oxide layer, b) react the oxide layer with gas of interest for pre-determined time (sensing electrode at open circuit), c) electrochemically regenerate the oxide layer by a potential sweep (sensing electrode back in circuit) and d) measure the current (charge) necessary to regenerate the oxide layer.

These steps are suitably controlled by electronic circuitry which includes a timing circuit to reproducibly place the sensing electrode in and out of circuit, in addition to standard potentiostatic and amplification circuitry. For measurement of the current necessary to regenerate the oxide layer (Step d), the current can be measured at a pre-determined time (seconds to minutes) after the electrode is placed back in circuit, or the current can be recorded and integrated. For the latter method, a device such as a microprocessor or computer can be used to store and integrate the data.

Typically, potentiodynamic operating conditions were an initial potential of +3 mV vs. a Pt/air reference electrode and a potentiodynamic timing cycle of 1 to 2 minute reaction time (sensing electrode at open circuit) and a regeneration time (sensing electrode in circuit) of 30 seconds. Initial potentials were varied over the range of +3 to +200 mV vs. the Pt/air reference. Open-circuit times varied over the range of 15 seconds to 5 minutes while in-circuit times of 20 and 30 seconds were used.

The following examples are provided to illustrate the sensor cell of the invention and should not be construed in limitation thereof.

EXAMPLE 1:

Sensor Cell Response to Hz/$N_2$- Pt Sensing Electrode

The response of an Hz sensor cell (Sensor Cell A) to 50, 100, and 200 ppb Hz in dry $N_2$ is shown in the graph of FIG. 2. The sensor cell tested had Pt black sensing, counter and reference electrodes, all intimately bonded to an anion-exchange membrane to form a unitized sensor cell and no liquid electrolyte was used. The upper curve 45 is for the peak response of the sensor cell operating in the potentiodynamic mode at an initial potential of +3 mV v. Pt/air with a timing sequence of 20 second reaction time/30 seconds in circuit. For comparison, the response curve 47 of the same sensor cell operating potentiostatically at +3 mV is also shown. FIG. 2 shows that the response to Hz in a potentiodynamic mode is nearly linear and is approximately 7 to 10 times higher than the potentiostatic response. The slope of the response in the potentiodynamic mode, 16.8 $\mu$A/ppm, is also significantly higher than that in the potentiostatic mode, 3.2 $\mu$A/ppm. The higher slope provides higher sensitivity. The significant enhancement of sensor cell sensitivity shown here is a major benefit of potentiodynamic operation.

EXAMPLE 2:

Hz/Air Testing - Pt Electrode

Concentrations of Hz in dry air and in dry $N_2$ were measured with a second sensor cell (Sensor Cell B) having the same configuration as Sensor Cell A. FIG. 3 compares the response of Sensor Cell B to Hz in dry $N_2$ and in dry air. The potentiodynamic operating conditions were the same as those employed in Example 1. The sensor cell response to a given concentration of Hz, after subtraction of the background response, was lower in air than in $N_2$ and the likely cause is discussed below. However, the sensor cell sensitivity is sufficient to detect 10 ppb Hz in air. This concentration would produce a response of approx. 0.2 $\mu$A, based on the Hz/air data presented in FIG. 3.

A likely cause of the decreased sensor cell response in air is chemical reaction of Hz with air at the surface of the Pt sensing electrode. The chemical reaction would compete with the electrochemical reaction of Hz, resulting in decreased sensor cell response. As mentioned above, Hz is known to be very reactive with air and this reaction can be catalyzed by Pt.

EXAMPLE 3:

Detection of $NH_3$—Pt Black Sensing Electrode

Sensor Cell B was evaluated for its response to 25 ppm $NH_3$/air. Potentiodynamic operating conditions were the same as those used in Example 1. Sensor Cell B had a net response of 30μA/ppm $NH_3$ in short-term testing, demonstrating the feasibility of detecting low levels of $NH_3$. With a Pt black sensing electrode, the level of sensor cell response is similar for Hz species and for $NH_3$.

EXAMPLE 4:

Detection of Hz Species—Gold Sensing Electrode

To improve the selectivity of the sensor cell for Hz species in the presence of $NH_3$ and to increase response to Hz species in air, a sensor cell (Sensor Cell C) with a gold, rather than Pt sensing electrode was tested. The sensing electrode had a very low loading of gold sputtered onto the membrane to form an integrally attached sensing electrode. Standard integrally bonded Pt black counter and reference electrodes were used. The unitized cell was tested in the potentiostatic mode at a potential of +3 mV vs. the Pt/air reference.

Figure 4:
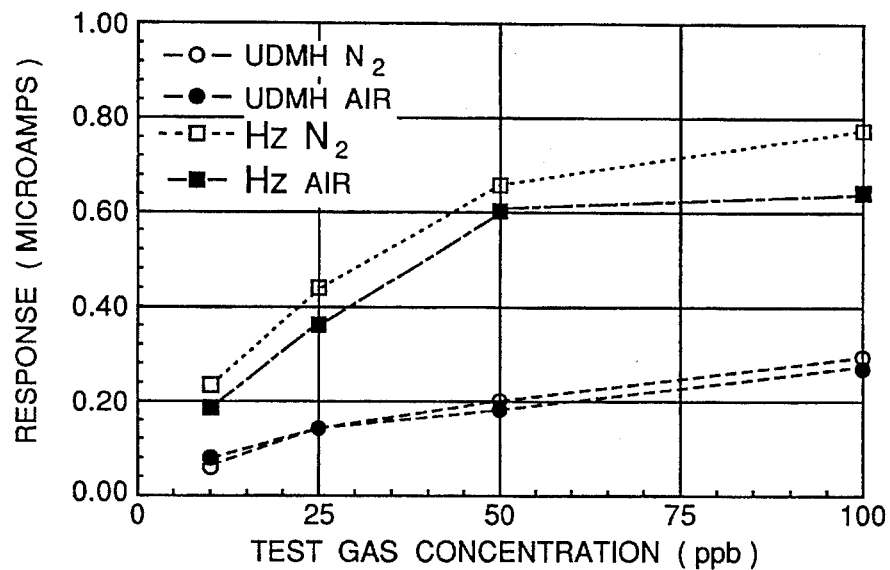
FIG. 4 is a graph of the responses of gas sensors with an Au sensing electrode to Hz and UDMH in $N_2$ and in air.

The response of the unitized sensor cell to Hz and UDMH in dry $N_2$ and dry air is shown in FIG. 4. Due to the use of gold sensing electrode, the response to Hz in $N_2$ is only slightly higher than the response to Hz in air, while response to UDMH is equivalent with air and $N_2$. It appears that the parasitic chemical reaction of Hz with air is significantly lower on a gold catalyst than on a Pt catalyst. Thus the gold sensing electrode is the more sensitive in Hz dectection.

FIG. 4 also shows that sensor cell response to Hz is somewhat higher than to the same concentration of UDMH. This is likely due to the difference in the electrochemical reaction mechanisms and kinetics of the two species. Sensor cell response to MMH is similar to that for Hz.

EXAMPLE 5:

Selectivity

Figure 5:
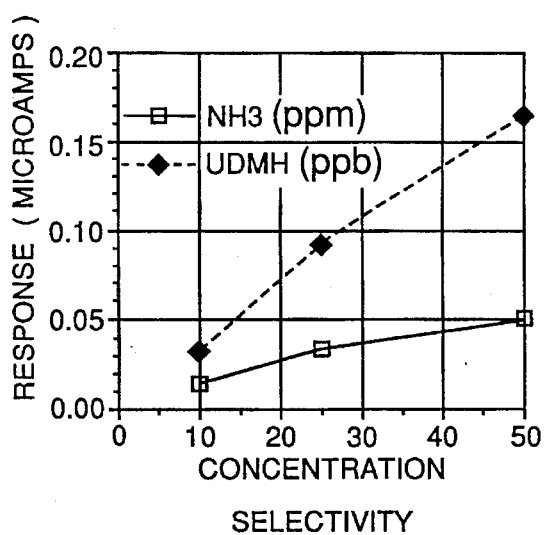
FIG. 5 is a graph of the response and selectivity of a gas sensor of the invention with an Au sensing electrode, to UDMH in the presence of $NH_3$.

In addition to minimizing Hz reaction with air, the gold electrode provides selectivity for Hz species v. $NH_3$. Thus FIG. 5 shows the response of Sensor Cell C to 10–50 ppb UDMH and to $NH_3$ in concentrations of 10–50 ppm. The sensor cell response (in μA/ppm) to UDMH is approximately 3000 times greater than the response to $NH_3$, which indicates strong selectivity of the gold sensing electrode to UDMH in the presence of $NH_3$. This is in contrast to the sensor cell with the Pt black sensing electrode of Example 3, for which the response to Hz and UDMH was nearly equivalent.

EXAMPLE 6:

Sensitivity of a Gold Sensing Electrode in Two Operating Modes

FIG. 6 is a graph showing the results obtained with a sensor cell having a gold-sensing electrode, operated in the potentiostatic (PS) and potentiodynamic (PD) modes. Thus as was indicated in FIG. 2, the PD mode of the sensor cell of the invention is the more sensitive of the two modes.

Thus the sensor cell of the invention can detect Hz type gases with ppb sensitivity and $NH_3$ with ppm sensitivity. The sensor cell of the invention which contains no liquid electrolytes is operated in two modes, as discussed above and can detect minute amounts of toxic gasses such as the hydrazines and ammonia.

The membrane of the gas sensor cell of the invention can be 1 to 20 mils thick and preferably is 2 to 10 mils thick (wet).

The membrane includes a hydrocarbon backbone, radiation grafted to a perfluorocarbon base film of, e.g. polytetrafluorethylene (PTFE), fluoroethylenepropulene (FEP) or polyvinylfluoride (PVF). The backbone can be of, eg. partially fluorinated or alkyl (eg. polystyrene) quartenary ammonium hydroxide.

The housing for the gas sensor cell of the invention can be of any suitable, durable and inert material such as polysulfone, polycarbonate, PTFE or FEP.

The housing for all components of the gas sensor of the invention can be of a moldable plastic, eg. a polyolefin or polystyrene.

The gas sensor of the invention with its electrical components shown in FIGS. 7 and 8, can be made in a compact lightweight package that fits, eg in a breast pocket or can otherwise be worn or carried by the user.

What is claimed is:

1. A gas sensor comprising,
   an electrochemical cell having
   a) an anion-exchange membrane,
   b) means to maintain said membrane hydrated,
   c) a reference electrode,
   d) a counter electrode;
   e) a sensing electrode and
   f) a gas inlet,
   said electrodes being spaced from each other and in contact with said membrane, said sensing electrode being mounted proximate said inlet to contact the gas to be detected.

2. The gas sensor of claim 1 wherein said electrodes are attached to said membrane and said membrane is a solid polymer electrolyte having negative ions therein.

3. The gas sensor of claim 2 wherein said membrane includes a hydrocarbon backbone grafted to a perfluorocarbon film.

4. The gas sensor of claim 2 having a gas outlet spaced from said inlet to admit alkaline reactive gas through said inlet to contact said sensing electrode and then to exit via said outlet in a normal gas diffusion process.

5. The gas sensor of claim 4 having a vacuum type pump attached to said outlet for drawing said gas more rapidly through said inlet to contact said sensing electrode and out said outlet for greater sensitivity in detection of said gas.

6. The gas sensor of claim 5 having a housing of inert material to contain said cell, power supply, electronic components and pump.

7. The gas sensor of claim 2 wherein said cell has a sensing electrode and membrane to detect hydrazine (Hz), Hz derivatives and ammonia ($NH_3$).

8. The gas sensor of claim 7 having a Pt sensing electrode for detection of $NH_3$.

9. The gas sensor of claim 2 wherein said reference electrode is of platinum black/air, said counter electrode is of platinum black and said sensing electrode has a catalyst selected from the group consisting of Pt black, gold, Ni, Pd, Au—Pt and carbon.

10. The gas sensor of claim 9 having a gold sensing electrode for detection of hydrazine (Hz) species.

11. The gas sensor of claim 2 having an anion-exchange membrane which includes a hydrocarbon backbone, radiation grafted to a perfluorocarbon film.

12. The gas sensor of claim 1, having a power supply and electronic components electrically connected to said sensing electrode and said counter electrode to measure an electric current therefrom when said sensing electrode is contacted by an alkaline reactive gas and means to measure said current to derive the concentration of said gas.

13. The gas sensor of claim 1 wherein said membrane is maintained hydrated.

14. A method for detecting gas with a gas sensor which includes an electrochemical cell having
   a) an anion-exchange membrane,
   b) means to maintain the membrane hydrated,
   c) a reference electrode,
   d) a counter electrode,
   e) a sensing electrode and
   f) a gas inlet proximate said sensing electrode, wherein said electrodes are spaced from each other and in contact with said membrane, which method comprises, contacting said sensing electrode with the gas to be detected, to cause a reaction in which OH⁻ ions migrate from said counter electrode through said membrane to said sensing electrode and cause a current to flow via an external conductor from sensing to counter electrodes and measuring said current to derive the amount of gas detected.

15. The method of claim 14 operated in the potentiostatic mode wherein said sensing electrode is held at a fixed potential with respect to said reference electrode at which said reaction of the gas to be detected occurs, measuring the current flowing between said sensing and counter electrodes from said reaction to determine the concentration of said gas.

16. The method of claim 14 wherein said sensing electrode is held at a fixed potential of between +3 mV to +200 mV with respect to the reference electrode, for detecting Hydrazine (Hz) species and $NH_3$.

17. The method of claim 16 wherein said sensing electrode is held at a fixed potential between +3 mV to +10 mV v. the reference electrode.

18. The method of claim 14 operated in the potentiodynamic mode comprising:
   a) holding the sensing electrode potential constant to form a well-defined potential-determined oxide layer,
   b) reacting said oxide layer with the gas to be detected for a predetermined time, with the sensing electrode at open circuit,
   c) electrochemically regenerating an oxide layer on said sensing electrode by connecting said electrode back into the circuit to effect a potential sweep and
   d) measuring the current flowing between said sensing and counter electrodes necessary to regenerate said oxide layer.

19. The method of claim 18 wherein said sensing electrode is held at a fixed potential in a range between +3 mV to +200 mV as against a Pt/air reference electrode, employing an open circuit time of 1–2 minutes and a closed circuit regeneration time of 25–35 seconds and then measuring the current necessary to regenerate said oxide layer to determine the concentration of the gas being detected.

20. The method of claim 19 using a Pt sensing electrode.

21. The method of claim 19 employing an Au sensing electrode.

22. The method of claim 19 employing an Au sensing electrode for selectivity in detecting a ppb concentration of UDMH in the presence of a ppm concentration of $NH_3$.

23. The method of claim 14 employed to detect hydrazine (Hz) species gases.

24. The method of claim 23 wherein OH⁻ ions migrate to said sensing electrode when Hz type gas is present according to:

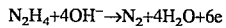
$$N_2H_4 + 4OH^- \rightarrow N_2 + 4H_2O + 6e$$

which causes said current to flow in said conductor for measurement of the concentration of said gas.

25. The method of claim 14 employed to detect concentrations of (Hz), unsymetricaldimethylhydrazine (UDMH) and monomethylhydrazine (MMH).

26. The method of claim 14 being used to detect the concentration of $NH_3$ in ppm.

27. The method of claim 26 wherein said OH⁻ ions migrate to said sensing electrode when ammonia is present according to:

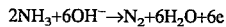
$$2NH_3 + 6OH^- \rightarrow N_2 + 6H_2O + 6e$$

which causes said current to flow in said conductor for measurement of the concentration of said ammonia.

28. The method of claim 14 using a Pt sensing electrode.

29. The method of claim 14 using an Au sensing electrode.

* * * * *